United States Patent
Ylitalo (10) Patent No.: US 8,605,356 B2
(45) Date of Patent: Dec. 10, 2013

(54) WINDOW FOR YEAR-ROUND SOLAR ENERGY CONSERVATION

(76) Inventor: Andrew Samuel Ylitalo, Stillwater, MN (US)

( * ) Notice: Subject to any disclaimer, the term of this patent is extended or adjusted under 35 U.S.C. 154(b) by 861 days.

(21) Appl. No.: 12/615,197

(22) Filed: Nov. 9, 2009

(65) Prior Publication Data
US 2011/0109957 A1    May 12, 2011

(51) Int. Cl.
*F21V 9/04* (2006.01)
*F21V 9/06* (2006.01)
*G02B 5/08* (2006.01)
*G02B 5/20* (2006.01)

(52) U.S. Cl.
USPC ............................................. 359/359

(58) Field of Classification Search
USPC ............ 359/359, 360; 454/69, 121, 122, 213
See application file for complete search history.

(56) References Cited

U.S. PATENT DOCUMENTS

| | | |
|---|---|---|
| 3,925,945 A | 12/1975 | White |
| 4,081,934 A | 4/1978 | Franz |
| 4,180,954 A | 1/1980 | Gell |
| 4,224,771 A | 9/1980 | Dunsmore |
| 4,235,048 A | 11/1980 | Gillery |
| 4,296,734 A | 10/1981 | Nevins |
| 4,320,155 A | 3/1982 | Gillery |
| 4,335,166 A | 6/1982 | Lizardo et al. |
| 4,365,620 A | 12/1982 | Bliamptis |
| 4,397,121 A | 8/1983 | Dunsmore |
| 4,459,975 A | 7/1984 | Hobart |
| 4,577,619 A | 3/1986 | Howe |
| 5,215,818 A | 6/1993 | Silver et al. |
| 5,398,446 A | 3/1995 | Kunert |
| 6,494,940 B1 * | 12/2002 | Hak ................................ 96/224 |
| 6,589,613 B1 | 7/2003 | Kunert |
| 7,057,805 B2 | 6/2006 | Phillips et al. |
| 7,270,600 B2 * | 9/2007 | Kim et al. ...................... 454/198 |
| 7,405,872 B2 * | 7/2008 | Simpson et al. ............... 359/359 |
| 2003/0012936 A1 | 1/2003 | Draheim et al. |
| 2005/0000642 A1 | 1/2005 | Everaerts et al. |
| 2006/0154049 A1 | 7/2006 | Padiyath et al. |
| 2006/0225353 A1 | 10/2006 | Erell |
| 2008/0092456 A1 * | 4/2008 | Millett et al. ........................ 52/1 |
| 2009/0158936 A1 | 6/2009 | Janssen et al. |

FOREIGN PATENT DOCUMENTS

| | | | |
|---|---|---|---|
| EP | 0922829 | | 6/1999 |
| GB | 2424449 A | * | 9/2006 |
| WO | 2009086053 | | 7/2009 |

* cited by examiner

*Primary Examiner* — Stephone B Allen
*Assistant Examiner* — Tamara Y Washington (57) ABSTRACT

A window for energy conservation in all seasons and a method of energy conservation using the window are described. The window operates as solar energy collector in winter and solar energy reflector in summer without using energy consuming devices such as pumps or fans. The window includes an optically transparent first component and a partially reflecting partially absorbing second component that is disposed close and parallel to the first component. The lateral separation between the first and second component can be changed from a smaller separation between the parallel first and second components to cool the room to a greater separation between the parallel first and second components to heat the room.

22 Claims, 6 Drawing Sheets

WINDOW FOR YEAR-ROUND SOLAR ENERGY CONSERVATION

FIELD OF THE DISCLOSURE

The present disclosure is directed to a window for saving energy in buildings year-round by functioning as a solar energy collector in a first position and by reflecting solar radiation in a second position, and to a method of saving energy using this window.

BACKGROUND

Windows on buildings and houses provide light into rooms and good view to the outside. However, heat from the sun easily enters and exits through windows, causing excess heating in the summer and constant heat loss in the winter. Also, sunlight causes glare and furniture fading inside rooms. For these problems, blinds or shutters are the common solution; however, they block outside view, which defeats the purpose of windows. Blinds and shutters also darken the room motivating people to turn on lights, increasing energy consumption.

To reduce this high energy consumption, different solutions exist, though most (if not all) are affected by the teeter-totter effect: energy savings in winter result in energy losses in summer, and vice versa. Some of these technologies inhibit the green house effect such as low-E (low-emissivity) glass where a surface of the Insulated Glass Unit (IGU) has an Infra-Red (IR) reflecting layer, typically in the form of silver metal coating. This technology reflects IR and some VIS (visible light), and keeps heat on the outside of buildings. However, low-E windows do not vary with the seasons and can not be applied to existing windows.

Other existing technologies used to reduce the energy consumption of buildings are based on electrochromic windows, such as those sold by Sage Glass. In the Sage electrochromic window, electric voltage is applied to darken the glass and block VIS and IR in the summer Like low-E, electrochromic glass can not be applied to existing windows. In addition, electrochromic windows are extremely expensive costing over $1,000 per window, and require electricity (more energy) to operate.

Another fenestration technology used to save energy is the tinted or mirrored window film. Those films are usually applied to windows to reduce glare and brightness of the sun and to reflect IR wavelengths, thereby reducing solar heat gain in the room as described in US2006/0154049 and U.S. Pat. No. 7,057,805. This solution can save on cooling costs in hot climates and is perfect for subtropical cities. However, window films reject solar radiation year-round, meaning colder climates lose valuable solar heating in winter, increasing heating costs for the building.

Novel window designs were proposed by Franz (U.S. Pat. No. 4,081,934), Gell (U.S. Pat. No. 4,180,954), and Gillery (U.S. Pat. No. 4,235,048) where an IR reflecting coating is applied to one surface of a sheet of glass and the window is rotated in its frame when the seasons change. This results in the IR reflecting coating facing outside in the summer, minimizing solar heat gain, and facing the inside of the room in the winter months reflecting IR back into the room. A different solution was proposed by Bliamptis (U.S. Pat. No. 4,365,620) where a reversible double pane window with one pane adapted to block IR radiation is described. The entire window is adapted to pivot about a horizontal axis allowing for solar heating in winter and cooling in the summer Erell (US2006/0225353) proposes a rotatable window pane assembly that provides year-round energy savings but requires moving a "solar energy absorbing" glass pane from the interior to the exterior of a building by rotating the window pane. Also, the proposed window pane assembly requires complex window design, can not be applied to existing windows, and exposes the absorbing glass pane to the harsh exterior elements.

Therefore, there exists a need for a year-round energy saving solution for windows where such a solution can be applied to both existing windows and new windows, and does not require rotation of the window in its frame.

SUMMARY

Here, an energy-saving solution, based on a seasonably adjustable window, is proposed. A solar energy absorbing component, such as solar control window film, was used in an innovative manner that saves energy in buildings year-round. Instead of using an adhesive to permanently attach window film to windows, a seasonably adjustable separation is created between the film and the window. In winter when solar heating is desired, the film is placed at a fixed distance away from the inside surface of the window.

In summer when solar heating is not wanted, the film is placed closer to the window so the window film is against the glass, and the separation between the film and the glass is eliminated. The solar energy absorbing window film may be flexible or rigid such as coated acrylic sheet or even a coated glass.

Optionally, the film can be in a frame that has holes in it so wooden dowels (or something similar) that allow optimum separation to be achieved could be placed in those holes and permanently attached to the window so the frame can be easily moved from summer mode to winter mode and vice versa. The frame could then be taken off and placed out of the way if it gets dark, too.

Figure 1A:
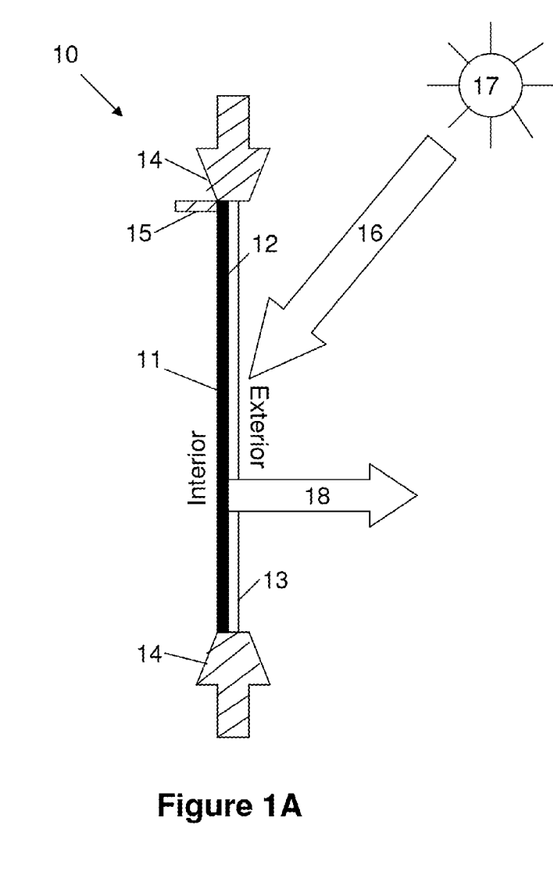
FIG. 1A shows the invention in summer mode.
Figure 1B:
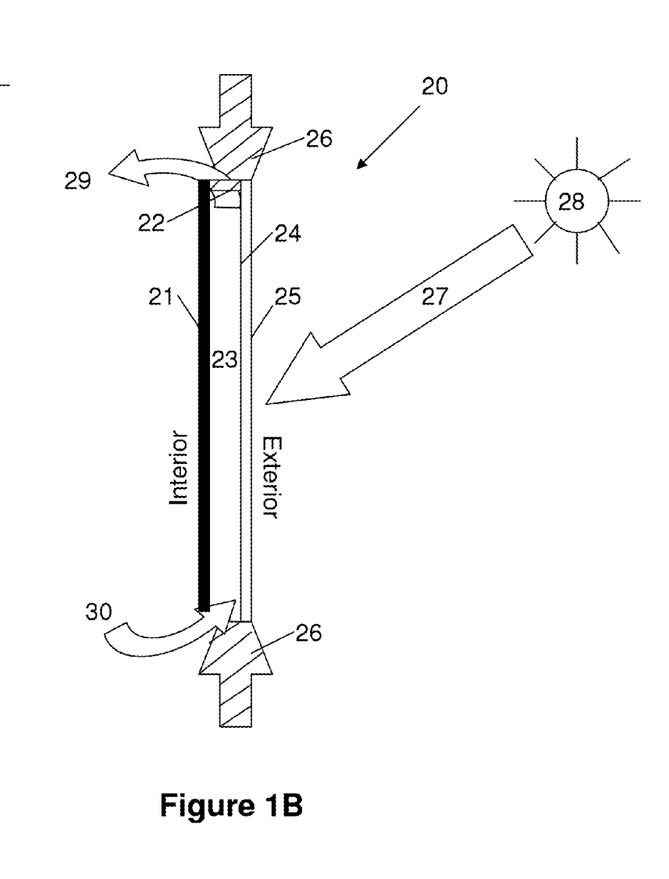
FIG. 1B shows the invention in winter mode.

Not wishing to be bound to any particular theory or model, it is believed that in the winter configuration, the separation between the film and the window forms an air channel, creating natural convection driven air circulation throughout the room. Natural convection causes warmer air to rise and cooler air to sink. As the film absorbs IR and VIS from solar radiation, it will reradiate most of these absorbed wavelengths in the form of IR back into the separation. This raises the temperature of the air in the separation, resulting in natural convection as shown in FIG. 1B. This warmer air is then transferred to the room through a top opening, supplementing the heating system. Subsequently, colder (and denser) air from the bottom of the room is taken in a bottom opening to be heated within the separation, and this cycle continues as it warms the entire room through natural convection. Optionally, thin, flexible plastic insulation can be attached to the sides to allow the air within the separation to heat up more efficiently from solar energy. In the summer, the film is placed directly on the window eliminating the separation as shown in FIG. 1A, so a large portion of the solar radiation will be either reflected or absorbed and reradiated back outside, keeping the room cool and reducing cooling costs.

In the first aspect of my invention, a window is described that includes an optically clear transparent first component facing the outside of a room and a partially reflecting partially absorbing second component facing the inside of a room. The two components are separated by an adjustable lateral separation, which provides for vertically upwards air flow from the bottom to the top of the window. In the summer, the lateral separation between the first and second components is eliminated, and in the winter the lateral separation is at least 1 cm, more preferably at least 5 cm, and most preferably at least 10 cm.

In the second aspect, optionally the window includes a UV germicidal lamp to purify the air circulating through the separation space between the two components as it exits the separation and enters the room, or as it enters the separation from the room.

In the third aspect, a method for saving energy is provided using the above described window.

The above summary of the present invention is not intended to describe each disclosed embodiment or every implementation of the present invention. The Detailed Description and Examples that follow more particularly exemplify these embodiments.

BRIEF DESCRIPTION OF THE FIGURES

FIG. 1 is a side view schematic illustration of the invention, where

FIG. 2 is a schematic diagram of the invention with UV lamp attachment, where

FIG. 3 is a schematic diagram of an exemplary window attachment system utilizing hooks.

FIG. 4 is a schematic diagram of two additional exemplary window attachment systems. FIG. 4A illustrates an attachment system utilizing dowels, while

ADVANTAGES OF THE INVENTION

This invention, unlike other incumbent technologies, has advantages year-round. In the winter, it eliminates glare from the sun without obstructing view, prevents furniture and carpet fading caused by UV radiation, and absorbs both IR and VIS radiated from the sun and reradiates them in the form of IR, heating the room and reducing energy costs. In the summer, in addition to eliminating glare and absorbing UV and thus preventing furniture and carpet fading, this invention reflects IR and partly absorbs VIS and reradiates it outside, which subsequently reduces cooling costs.

My invention does not require complex window design, can be applied to existing windows, does not require rotation of the window, and because the partially reflecting partially absorbing component is always located in the interior of the room, it is not exposed to the outdoors, preventing weather induced degradation.

DEFINITIONS

As used herein, the term "partially reflecting partially absorbing component" or PRPAC refers to a component of the window that can absorb and/or reflect a portion of the sun's electromagnetic spectrum.

As used herein, the term "partially absorbing" refers to a window glazing component that absorbs 30-80% of the visible spectrum of the sun, defined as having wavelength between 400 and 700 nanometers.

As used herein, the term "optically transparent" refers to a window glazing component that absorbs less than 20% of visible light.

As used herein, the term "attachment system" refers to a mechanical device connecting one or more window glazing components to a window frame.

As used herein, "flexible" indicates a sheet that can be bent around a cylinder at least 100 cm in diameter.

As used herein, a "heating degree day" indicates a day of the year on which the heating system is used to heat a building in a location. Typically, these days are colder days that occur in late fall, winter, or early spring, depending on the climate.

As used herein, a "cooling degree day" indicates a day of the year on which the air-conditioning or cooling system is used to cool a building in a location. Typically, these days are warmer days that occur in late spring, summer, and early fall, depending on the climate.

"Heat transfer" as used herein, refers to one or more of conduction, convection or radiation, or a combination thereof.

"Conduction" is the method of heat transfer through solid materials where the heat is transferred molecule to molecule. An example of this occurs when heating a metal rod. While the end near the heat source gains thermal energy, molecules at that end vibrate faster, eventually causing molecules across the entire metal rod to vibrate faster. This results in warmer temperatures even at the end furthest away from the heat source.

"Convection" is the method of heat transfer through fluids where the fluid moves away from the heat source carrying thermal energy along with it. An example of this would occur when boiling water. The warmer water near the burner becomes less dense and rises to the top while being replaced by cooler water near the bottom.

"Radiation" is a method of heat transfer through electromagnetic (EM) waves. The heat source emits EM waves that cause other objects to gain thermal energy. An example of this occurs at the sun. The sun emits EM waves including IR waves, which help to heat the earth.

DETAILED DESCRIPTION

The invention relates to a novel window for buildings to improve solar energy management. The window comprises an optically transparent component such as a glass sheet, and a PRPAC component, which acts as a solar energy collector when separated from the optically transparent component by an air gap, and as a solar protection when the separation between the two components is eliminated. This concept becomes clear when described in reference to FIG. 1.

FIG. 1 illustrates the window of the invention. In FIG. 1A, the summer mode 10 is illustrated, and in FIG. 1B, the winter mode 20 is illustrated. To simplify the diagram, only the interior pane of a single, double or triple pane glass window is shown. Describing the summer mode 10 in FIG. 1A, the system includes a partially reflecting partially absorbing component (PRPAC) 11, placed directly on the interior surface 12 of the optically transparent window glass 13. The window is encased in a window frame 14. To simplify the diagram, only cross-sections of the head and sill are shown. The PRPAC is slidably mounted onto the window frame by an attachment system 15. During the day, radiation 16 from the sun 17 is partially reflected 18 and partially absorbed by the PRPAC, resulting in a cooler room. Describing the winter mode 20 in FIG. 1B, the partially reflecting partially absorbing component (PRPAC) 21, is movable along the attachment system 22 towards the interior of the room and away from the optically transparent window glass, creating a separation gap 23 between the PRPAC 21 and the optically transparent interior surface 24 of the window glass 25. The window is encased in a window frame 26. During the day, radiation 27 from the sun 28 penetrates through the optically transparent window glass and is partially reflected by the PRPAC into the separation gap 23. Another part of the solar radiation is absorbed by the PRPAC and subsequently reradiated in the form of long-wave radiation into the separation space. This long-wave radiation remains in the gap and does not penetrate the glass of the window as known from the greenhouse effect. This results in the heating of the air in the separation gap, which rises to the top of the window because of natural convection, and exits the separation out a top opening as shown by arrow 29. The denser, cool air from the room replaces the rising warm air by entering the separation as shown by arrow 30. Thereby the air circulation increases the overall temperature of the room, reducing the energy required to heat the room.

The PRPAC can be rigid or flexible. Typically, the PRPAC contains visible light absorbing particles such as carbon black, and it appears dark in color. Preferably, the PRPAC reflects IR radiation by having IR filter such as a metal coating; and it absorbs part of the visible spectrum by containing light absorbers such as carbon black. For example, some suitable PRPACs for this invention are sold under the trade names Night Vision™ and Prestige™, both available from 3M Corporation (St. Paul, Minn.) and as well as under the name CP Films™ available from CP Films Inc. (Martinsville, Va.).

The separation between the PRPAC and the optically transparent component is preferably at least 1 cm, more preferably at least 5 cm, and most preferably the separation is at least 10 cm.

This invention can be easily adapted to existing IGUs (insulated glass unit) in buildings, and it can be installed independently from the IGU as an after market option.

Figure 2A:
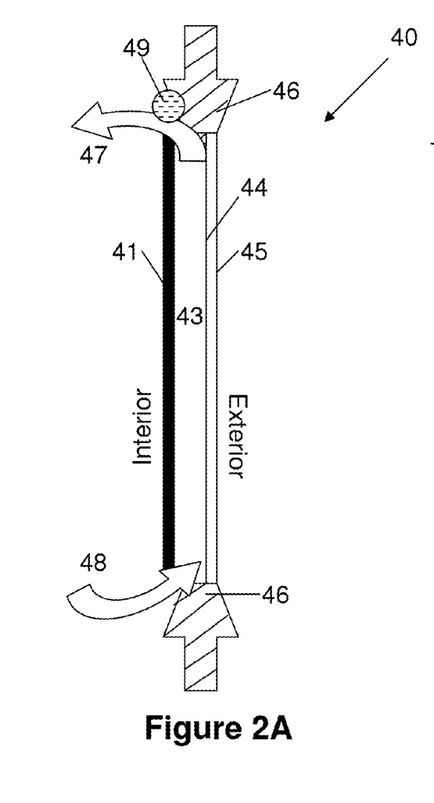
FIG. 2A is a side view and FIG. 2B is a top view.
Figure 2B:
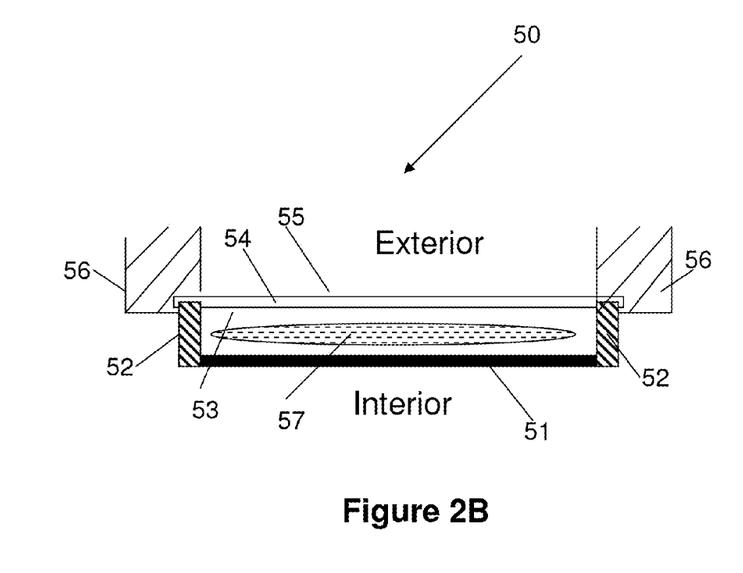

In one embodiment the window of this invention may comprise an ultraviolet (UV) light source placed at the top or at the bottom of the window between the optically transparent window glass and the PRPAC as shown in FIG. 2 (where only the embodiment with the lamp at the top is shown), where the air that circulates through the separation gap will at least partially get exposed to the germicidal UV radiation. FIG. 2A provides a schematic side view of the invention in the winter mode with the optional UV lamp. In diagram 40, the partially reflecting partially absorbing component 41 and the optically transparent component 45 are separated by a gap 43. The window is encased in a window frame 46. The heated air in the separation rises to the top of the window and exits the separation as shown by arrow 47. The cool air from the room replaces the rising warm air by entering the gap as shown by arrow 48. The air stream exiting the gap is exposed to radiation from UV lamp 49. A top view schematic of the invention in the winter mode with the optional UV lamp is shown in FIG. 2B. In diagram 50, the PRPAC 51 is connected to the window frame 56 using attachment system 52 creating a separation 53 between PRPAC and the interior surface 54 of the window glass 55. The window is encased in a window frame 56. The UV lamp 57 is positioned between the window glass 55 and the PRPAC 51 so as to expose the hot air exiting the gap at the top of the window to UV radiation from the lamp.

It is known that ultraviolet (UV) light can be used to destroy pathogens such as bacteria, viruses, and mold spores. Exposure to a sufficient dose of UV light kills bacteria and deactivates many other organisms including viruses. Therefore, the UV light source can help disinfect the air in the room when coupled with the window described in the current invention.

UV light is part of the sun's electromagnetic spectrum, and the short wavelength portion, known as UV-C (from about wavelength of 100 nanometers to about 300 nanometers) is germicidal. UV-C destroys microorganisms by causing damage to the polynucleotides preventing DNA and RNA replication, and rendering the microorganisms unable to reproduce and function. Commercially available UV light sources can be obtained for example from Fusion Systems, Inc. (Gaithersburg, Md.). Especially useful are UV sources equipped with H-bulb having emission range between 210 and 315 nm.

It is important to direct the UV light away from the parts of the room where people may be; therefore, it is desirable to position the lamp so that the emitted UV radiation is directed towards the top of the room.

As the air from the room enters or exits the separation, depending on the chosen location of the UV lamp, it is exposed to UV radiation from the lamp, which disinfects the air. Germicidal UV lamps produce short wavelength radiation that has antimicrobial effects, and such lamps have been used as means to disinfect air as described in US 2009/0158936.

In the summer mode where the separation is eliminated, the PRPAC can be attached to the optically transparent component, for example the interior of the window glass by various means. For example, it can be attached using an adhesive such as pressure sensitive adhesive, or it can be attached using electrostatic forces such as those used to attach decorative vinyl decals to glass.

In some embodiments the PRPAC can be attached to the surface of the window glass (in the summer mode) by adhesive means. An adhesive layer can be applied to the glazing component to provide secure attachment to the glass surface while also being removable under moderate force without leaving a residue on the glass (e.g., removable and/or repositionable pressure sensitive adhesives, PSAs). Examples of suitable adhesives include those based on acrylates, urethanes, silicones, epoxies, rubber based adhesives (including natural rubber, polyisoprene, polyisobutylene, and butyl rubber, block copolymers, and thermoplastic rubbers), and combinations thereof.

As used herein and in the appended claims, an adhesive is considered to be "removable," if the removable pressure sensitive adhesive has a 180 degree peel strength (from a painted steel substrate employing a peel rate of 30.5 cm/min) of less than 8 N/cm, and more preferably less than 6 N/cm.

As used herein and in the appended claims, "repositionable" refers to the ability to be, at least initially, repeatedly adhered to and removed from a surface or substrate without substantial loss of adhesion capability. In some embodiments, the repositionable pressure sensitive adhesive has a peel strength, at least initially, to the substrate surface lower than that for a conventional aggressively tacky PSA.

Examples of suitable removable and repositionable pressure sensitive adhesives include those adhesives based on solid inherently tacky, elastomeric microspheres, such as those disclosed in Silver (U.S. Pat. No. 3,691,140).

In some embodiments, the PRPAC has electrostatic cling properties, having a permanent electrostatic charge and generally exhibiting electrostatic attraction to a wide variety of surfaces thereby allowing the PRPAC to be removably adhered to the glass surface in the summer mode. Permanent electrostatic charge can be imparted to the PRPAC using corona charging (nitrogen or air) as described in US 2005/0000642. In some embodiments, the adhesive maybe optionally combined with electrostatic charge to provide better adhesion and repositioning of the PRPAC to the optically transparent component of the window.

If an adhesive is used to attach the PRPAC to the optically transparent component, the adhesive must exhibit sufficient optical quality and light stability such that the adhesive material does not yellow with time or upon weather exposure so as to degrade the viewing quality through the window. The adhesive material may be applied using a variety of known coating techniques such as transfer coating, knife coating, spin coating, die coating and the like. Additional examples of suitable adhesive materials for use in the adhesive layer include those described in Draheim et al. (US2003/0012936). Several of such adhesive materials are commercially available under the trade designations "8141", "8142", and "8161" adhesives from 3M Corporation, St. Paul, Minn.

Figure 3A:
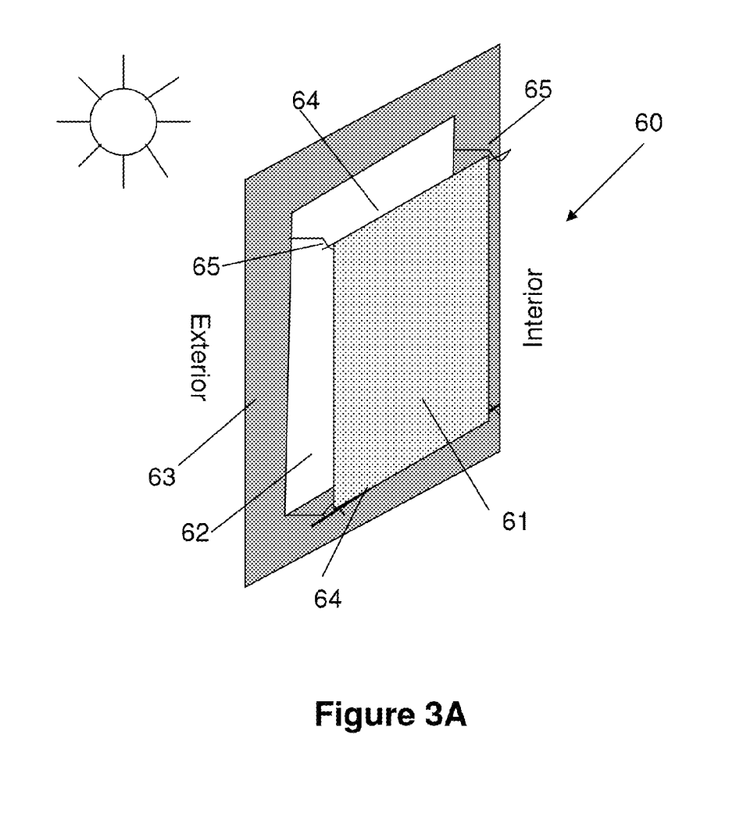
FIG. 3A illustrates the winter mode.
Figure 3B:
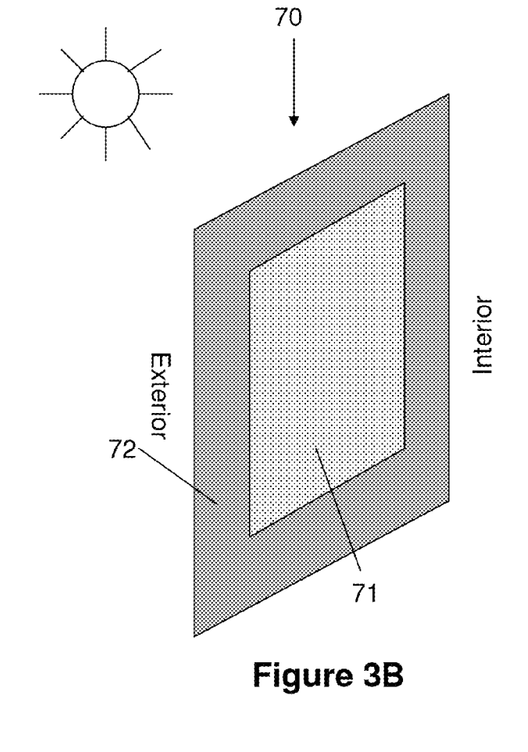
FIG. 3B illustrates the summer mode.

The PRPAC can move between the summer and winter positions by any mechanical means. By way of example, the PRPAC can be placed parallel to the optically transparent component of the window by means of an attachment system comprising indented hooks as shown schematically in FIG. 3A. Referring to FIG. 3A, diagram 60 illustrates PRPAC 61 fixed parallel to the window glass 62, which is encased in the window frame 63. Rods 64 at the top and bottom hold the PRPAC onto hooks 65 attached to the window frame at each corner. This combination results in a separation between the window glass and the PRPAC in the winter. The hooks are positioned at the corners of the PRPAC so as to not block air circulation in and out of the separation gap. In the summer, the PRPAC is detached from the hooks and adhered to the window glass directly as illustrated in FIG. 3B. Referring to diagram 70, the PRPAC 71 is adhered to the window glass, which is encased in window frame 72. The rods and hooks are optionally removed and stored for later use. Secured pivots or other means of adhering rods to hooks can be used. One can envision hooks that rotate 90° upward to bring the PRPAC to the window glass eliminating the separation gap.

Figure 4A:
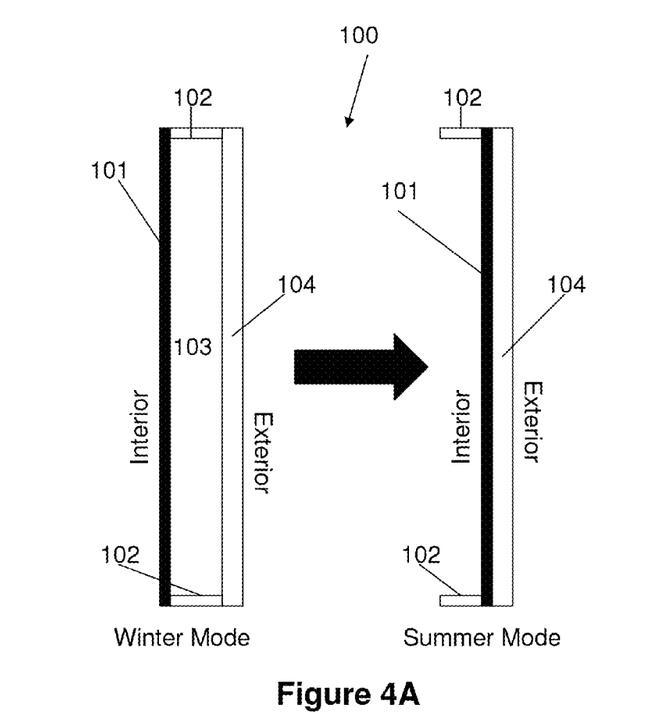

An alternative attachment system is shown in FIG. 4A. A schematic side view is illustrated in diagram 100 where the PRPAC 101 is mounted onto dowels 102 which are attached to the window frame. In the winter mode, the dowels provide for separation 103 between the PRPAC 101 and the optically transparent glass surface of the window 104. Optional indentations (not shown) in the dowels allow for precise control of the separation size. In the summer mode, the PRPAC 101 slides along the dowels 102 towards the optically transparent glass component 104 eliminating the separation and positioning the PRPAC on the glass. Also, this embodiment allows for the removal of the PRPAC from the dowels if no stoppers are used.

Figure 4B:
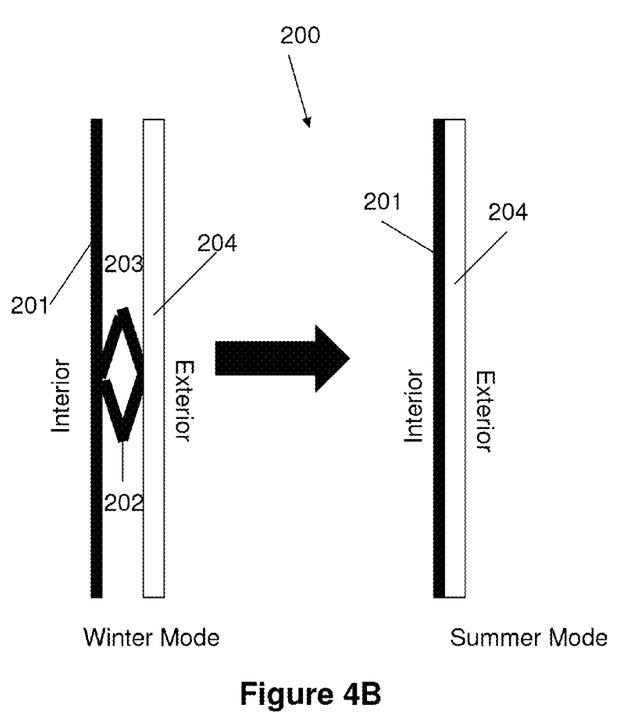
FIG. 4B illustrates an attachment system utilizing a scissor hinge concept.

Yet another alternative attachment system is shown in FIG. 4B. A schematic side view is illustrated in diagram 200 where the PRPAC 201 is separated from the window with a scissor hinge assembly 202 which is connected to the window frame in at least one place. In winter mode, the scissor shaped hinges provide for a separation 203 between the PRPAC 201 and the optically transparent glass component of the window 204. In summer mode, the PRPAC 201 is moved towards the optically transparent glass 204 eliminating the separation. The scissor hinge assembly folds and retracts into a suitable recess within the window frame (not shown).

The foregoing describes the invention in terms of embodiments foreseen by the inventor for which an enabling description was available, notwithstanding that insubstantial modifications of the invention, not presently foreseen, may nonetheless represent equivalents thereto.

EXAMPLES

The invention is further illustrated in the following illustrative examples.

Examples 1-4 and Comparative Example 1C

Figure 5:
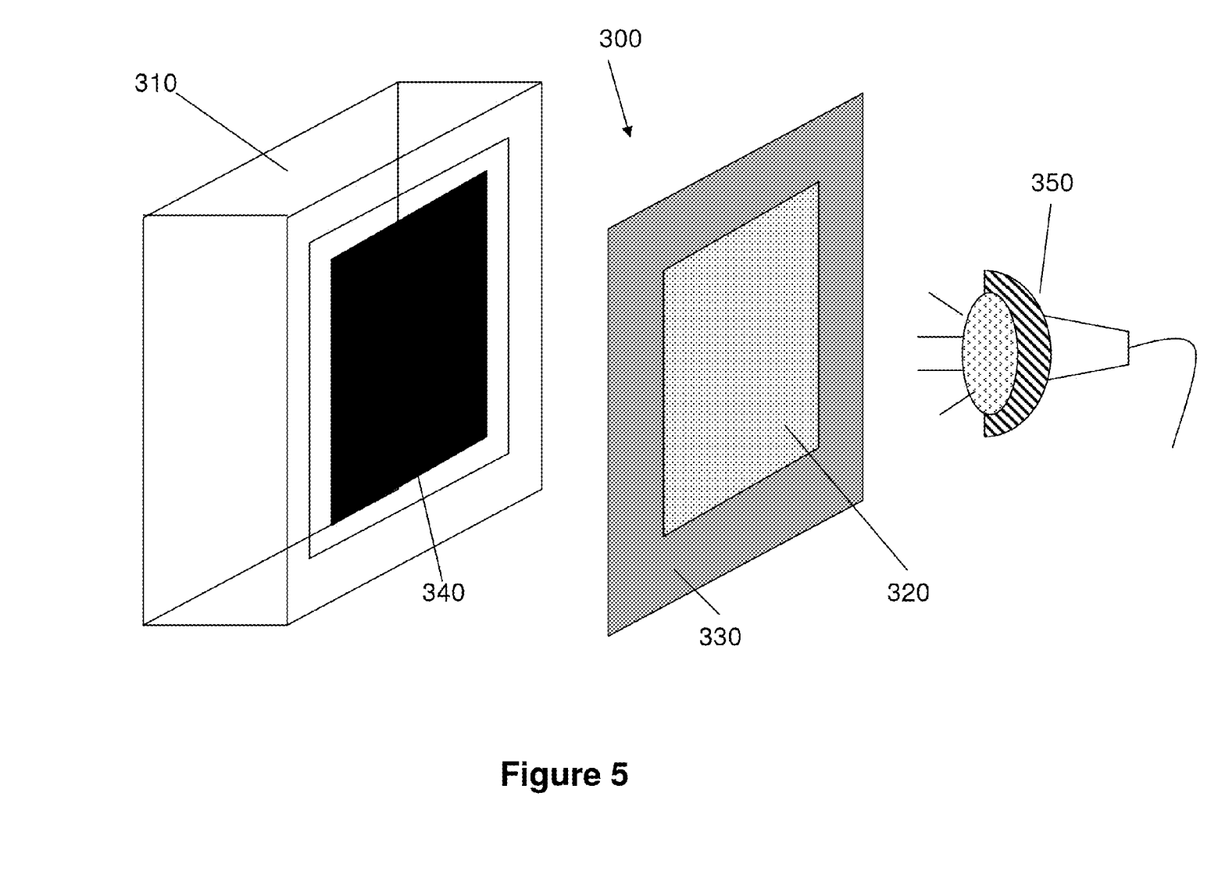
FIG. 5 is a diagram of the apparatus used to validate the invention.

An insulated box simulating a room was constructed with a removable framed glass as shown in FIG. 5. Apparatus 300 comprises a wood frame 310 measuring 43 cm by 33 cm by 28 cm (H×W×D) in size with 4 cm thick Styrofoam insulation applied to the walls of the box. One side of the box was removable and made of glass 320 encased in a wood frame 330. A K type thermocouple to measure room temperature was placed in the back of the box and shielded by a card wrapped in aluminum foil to simulate shade. The K type thermocouple was attached to a dual channel digital thermometer available from VWR Scientific Lab Stock Catalog. The PRPAC was a flexible film 340 attached inside the box with toothpicks that simulate the attachment system. The toothpicks were inserted into predrilled holes in the side walls of the box. In the winter mode, the film was placed at a distance of 5 cm from the glass. In the summer mode, the film was attached to the glass using double stick tape.

The partially reflecting partially absorbing components used in the examples were commercially available window films obtained from 3M Corporation (Saint Paul, Minn.). Table 1 lists the films used in each example.

TABLE 1

Films used in the examples.

| Example | Film Designation | Description |
|---|---|---|
| 1 | Prestige ™ 40 | Non-metalized solar control film, 40% transmission |
| 2 | Prestige ™ 50 | Non-metalized solar control film, 50% transmission |
| 3 | Prestige ™ 70 | Non-metalized solar control film, 70% transmission |
| 4 | RE35AMARL | Metal coated, IR reflecting solar control film, 35% transmission |
| 1C | No film | No film was used for the comparative example |

Each of the 4 window films were tested in two different configurations: applied directly to the glass surface of the window (summer mode) and separated by a gap of 5 cm from the interior glass surface to the film (winter mode). The sun was simulated by a lamp 350 equipped with 125 Watt Phillips light bulb (available from Menard's Hardware Stores). The lamp was set at a constant distance of 23.5 cm away from the window. It was then turned on, and the temperature in the back of the test room was measured as a function of time. In the winter mode configuration, a second thermocouple probe was used to measure the temperature in the separation gap simultaneously as a function of time.

Figure 6:
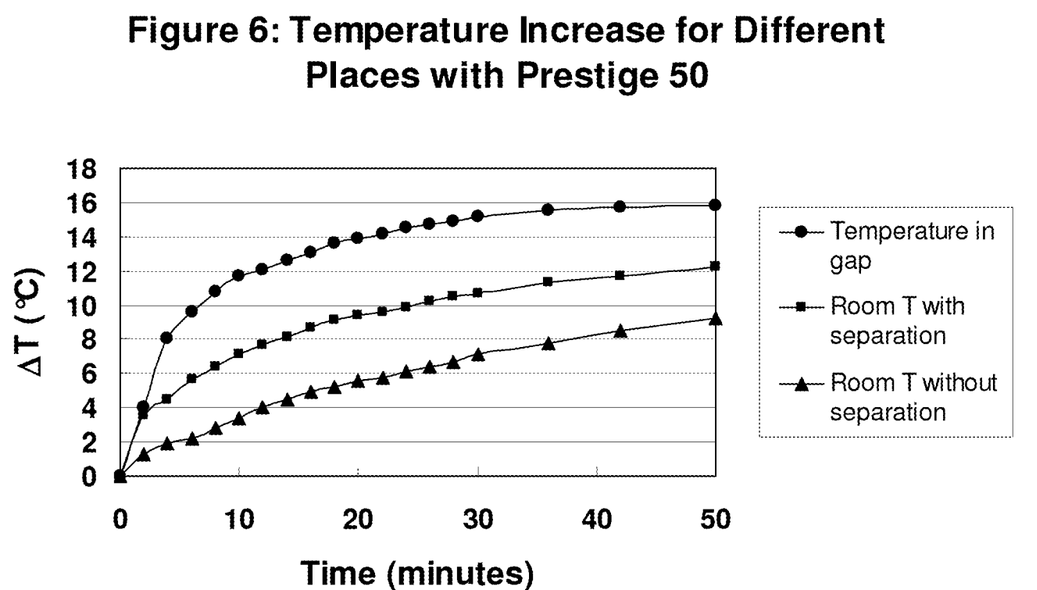
FIG. 6 is a graph showing temperature increase as a function of time.

The increase in temperature from a baseline value at the start of the experiment was measured every two minutes and plotted as a function of time. In all examples (except for the control example) the presence of a separation between the film and the glass resulted in a greater temperature increase in the box than that which resulted from having no presence of a separation. A sample graph for Prestige™ 50 film is shown in FIG. 6 where the rise in temperature in the box and in the separation gap (winter mode) as a function of time is shown. It is clear that when the film was applied directly on the glass (summer mode) the temperature in the room did not rise nearly as much as when the film was separated from the glass by a gap (winter mode). Also, the temperature in the separation gap in the winter mode was significantly higher than the room temperature, validating the concept of this invention.

Average results for the temperature increase after 50 minutes are given in Table 2. These experiments were repeated at least three times to obtain an average and standard deviation of the data. Prestige™ 40 with separation gap showed the highest temperature increase of all the films, while RE35AMARL (metal-coated) on the window showed the least temperature increase. For the Prestige™ series of films, the lower the light transmission of the film, the greater the difference in temperature increase was between the winter and summer modes. The control example with no film had a lower temperature increase than the Prestige™ 40, 50, and 70 with separation, and a higher temperature increase than the Prestige™ series films and the metal-coated film without a separation.

TABLE 2

Results for examples 1-4 and 1C.

| Example (film type) | Temperature increase, ΔT (° C.) | |
|---|---|---|
| | Winter Mode (with separation) | Summer Mode (no separation) |
| 1 (Prestige ™ 70) | 13.2 +/− 0.9 | 11.3 +/− 0.7 |
| 2 (Prestige ™ 50) | 12.4 +/− 0.9 | 10.8 +/− 0.1 |
| 3 (Prestige ™ 40) | 15.2 +/− 1.9 | 9.6 +/− 0.9 |
| 4 (RE35AMARL) | 11.5 +/− 0.2 | 8.0 +/− 0.3 |
| 1C (no film) | 12.1 +/− 1.3 | |

Example 5

Natural Convection Validation

A natural convection validation experiment was done by covering the top 20 cm of the glass window with a sheet of insulating cardboard material while exposing 16.5 cm of the window glass at the bottom. The lamp was "aimed" towards the bottom of the window where there was no cardboard insulation obstructing its radiation. Prestige™ 70 film with separation from the glass was used along with no film for control. The results of this experiment showed that when no window film was used, the top of the room heated up much more quickly than the bottom part, an expected outcome because the hot air is expected to rise to the top of the box and remain there. However, when the Prestige™ 70 with separation from the glass was used, the temperatures at the top and bottom halves of the room increased equally showing that natural convection resulted in air circulation throughout the room eliminating temperature gradients within the room.

Example 6

To measure energy savings, a MINCO polyimide flexible heater 12.7 cm by 12.7 cm (available from Minco, Minneapolis, Minn.) was placed at the bottom of the box on a layer of insulation. Prestige™ 40 film was applied to the window with and without separation and a DC power supply was used to drive the heater at 20 volts and 2.165 amps. Starting from a baseline temperature, the MINCO heater was turned on and allowed to heat the box 5° C. After that, a stopwatch was started and the lamp turned on simultaneously. The times it took to heat the room another 10° C. and 20° C. were recorded. Each experiment was repeated 5 times, and the average calculated. It was found that for the Prestige™ 40 it took 1.55 times longer to heat the room to the same target temperature when the film was applied directly on the glass (summer mode) than when the film was separated from the glass by 5 cm of air (winter mode). This result validates the usefulness of this invention: a window having an optically transparent component, such as a glass pane, and a partially reflecting partially absorbing component such as a solar control window film separated with a gap gives heating energy savings in winter.

The energy output of the heater was calculated using the Fourier Law of thermal conductivity: Q=VA (Q is watts, V is voltage, and A is amps). Using V=20 volts and A=2.165 amp resulted in Q of 43.2 watts or 0.0432 KW·h.

I claim:

1. A window utilizing solar heat for energy conservation comprising:
    an optically transparent first component configured to face an outside of a room; and
    a partially reflecting partially absorbing second component configured to face an inside of a room and disposed proximate and parallel to the first component, wherein the window is configured so that a lateral separation between the parallel first and second components can be changed from a smaller separation between the parallel first and second components to cool the room to a greater separation between the parallel first and second components to heat the room, the lateral separation between the parallel first and second components providing a passage for vertically upwards air flow from a lower portion of the window to an upper portion of the window.

2. The window of claim 1 where the partially reflecting partially absorbing component is a flexible film.

3. The window of claim 1 wherein the separation is at least one cm.

4. The window of claim 1 wherein the separation is at least five cm.

5. The window of claim 1 wherein the separation is at least ten cm.

6. The window of claim 1 where the passage between the partially reflecting partially absorbing component and the optically transparent component is substantially sealed along the vertical edges of the passage.

7. The window of claim 1 where the partially reflecting partially absorbing component is connected to the optically transparent component by an attachment system.

8. The window of claim 7 where the attachment system comprises dowels positioned at the corners of the window frame holding the partially reflecting partially absorbing component, wherein the partially reflecting partially absorbing component can slide along the dowels changing the separation between the first and the second component.

9. The window of claim 7 where the attachment system comprises indented hooks positioned at the corners of the window frame holding the partially reflecting partially absorbing component.

10. The window of claim 7 where the attachment system comprises scissor-shaped hinges positioned along a window frame holding the partially reflecting partially absorbing component.

11. The window according to claim 1 or claim 2 where when the separation is zero, the partially reflecting partially absorbing component is attached to the optically transparent component by adhesive means.

12. The window according to claim 1 or claim 2 where when the separation is zero, the partially reflecting partially absorbing component is attached to the optically transparent component by electrostatic means.

13. The window according to claim 1 further comprising a germicidal UV lamp mounted at the top or bottom of the window adjacent to the separation wherein at least part of the air moving through the separation contacts the UV radiation from the UV lamp.

14. A method for utilizing solar heat for energy conservation comprising the steps of:
providing a window comprising an optically transparent first component configured to face an outside of a room; and a partially reflecting partially absorbing second component configured to face an inside of a room and disposed proximate and parallel to the first component, wherein the window is configured so that a lateral separation between the first and second components can be changed from a smaller separation between the parallel first and second components to cool the room to a greater separation between the parallel first and second components to heat the room, the lateral separation between the parallel first and second components providing a passage for vertically upwards air flow from a lower portion of the window to an upper portion of the window,
applying a measurable lateral separation between the two components during heating degree days, and
eliminating the lateral separation between the two components during cooling degree days.

15. The method of claim 14 where the partially reflecting partially absorbing component is a flexible film.

16. The method of claim 14 wherein the separation is at least one cm.

17. The method of claim 14 wherein the separation is at least five cm.

18. The method of claim 14 wherein the separation is at least ten cm.

19. The method of claim 14 where the passage between the partially reflecting partially absorbing component and the window is substantially sealed along the vertical edges of the passage.

20. The method of claim 14 where when the separation between the two components is zero, the partially reflecting partially absorbing component is attached to the optically transparent component by adhesive means, electrostatic means, or combination thereof.

21. The window of claim 1 not comprising any energy consuming devices to provide vertically upwards flow from the lower portion of the window to the upper portion of the window.

22. The window of claim 1, wherein the lateral separation between the parallel first and second components can be changed from about zero to at least 15 cm.

* * * * *